(12) United States Patent
Lipes et al.

(10) Patent No.: US 8,420,330 B2
(45) Date of Patent: Apr. 16, 2013

(54) DIAGNOSIS AND TREATMENT OF CARDIAC TROPONIN 1 (CTN1) AUTOANTIBODY-MEDIATED HEART DISEASE

(76) Inventors: Myra A. Lipes, Brookline, MA (US); Lizbeth Cornivelli, Medford, MA (US)

(*) Notice: Subject to any disclaimer, the term of this patent is extended or adjusted under 35 U.S.C. 154(b) by 0 days.

(21) Appl. No.: 13/184,115

(22) Filed: Jul. 15, 2011

(65) Prior Publication Data

US 2013/0017192 A1    Jan. 17, 2013

(51) Int. Cl.
*G01N 33/53* (2006.01)
(52) U.S. Cl.
USPC ........ 435/7.1; 435/7.92; 424/184.1; 424/804; 514/16.4
(58) Field of Classification Search ........................ None
See application file for complete search history.

(56) References Cited

U.S. PATENT DOCUMENTS

| 7,407,767 | B2 |   | 8/2008 | Honjo et al. |
| 7,776,605 | B2 | * | 8/2010 | Mattingly et al. ................ 436/8 |
| 2004/0202658 | A1 |   | 10/2004 | Benyunes |
| 2005/0271658 | A1 |   | 12/2005 | Brunetta et al. |
| 2006/0246525 | A1 | * | 11/2006 | Honjo et al. ................ 435/7.93 |
| 2007/0172888 | A1 |   | 7/2007 | Hallermayer et al. |
| 2008/0102481 | A1 |   | 5/2008 | Mattingly et al. |
| 2008/0305512 | A1 |   | 12/2008 | Mattingly et al. |

FOREIGN PATENT DOCUMENTS

| WO | WO 9717980 A1 * | 5/1997 |
| WO | WO 2009118185 A1 * | 10/2009 |

OTHER PUBLICATIONS

Cunningham et al., J Clin Pathol. Feb. 2006;59(2):121-9.*
Touma et al., Joint Bone Spine 2008, 75:334-337.*
Printout from NCBI protein concerning homo sapiens cardiac troponin I, dated Aug. 6, 2012.*
Beck et al., "M-type phospholipase A2 receptor as target antigen in idiopathic membranous nephropathy," N. Engl. J. Med., 361(1):11-21 (2009).
Bhol et al., "Correlation of peptide specificity and IgG subclass with pathogenic and nonpathogenic autoantibodies in pemphigus vulgaris: a model for autoimmunity," Proceedings of the National Academy of Sciences of the USA, 92(11)5239-5243 (1995).
Cetta and Michels, "The autoimmune basis of dilated cardiomyopathy," Ann. Med., 27:167-173 (1995).
Engel et al., "Therapeutic targeting of B cells for rheumatic autoimmune diseases," Pharmacol Rev., 63(1):127-156 (2011).
Felker et al., "The spectrum of dilated cardiomyopathy. The Johns Hopkins experience with 1,278 patients," Medicine, 78(4):270-283 (1999).
Haralambous et al., "Increased natural autoantibody activity to cytoskeleton proteins in sera from patients with necrobiosis lipoidica, with or without insulin-dependent diabetes mellitus," Autoimmunity, 20(4):267-275 (1995).

Huang et al., "Rituximab specifically depletes short-lived autoreactive plasma cells in a mouse model of inflammatory arthritis," Proc. Natl. Acad. Sci. USA, 107(10):4658-4663 (2010).
Joly et al., "A single cycle of rituximab for the treatment of severe pemphigus," N. Engl. J. Med., 357 (6):545-552 (2007).
Kaya et al., "Identification of cardiac troponin I sequence motifs leading to heart failure by induction of myocardial inflammation and fibrosis," Circulation, 118(20):2063-2072 (2008).
Leandro et al., "Reconstitution of peripheral blood B cells after depletion with rituximab in patients with rheumatoid arthritis," Arthritis Rheum., 54(2):613-620 (2006).
Miettinen et al., "Clinical significance of troponin I efflux and troponin autoantibodies in patients with dilated cardiomyopathy," J. Card. Fail., 14(6):481-488 (2008).
Niebroj-Dobosz et al., "Circulating autoantibodies to troponin I in emery-Dreifus muscular dystrophy," Acta. Myol., 27:1-6 (2008).
Niebroj-Dobosz et al., "Evidence for autoimmunity to heart-specific antigens in patients with Emery-Dreifuss muscular dystrophy," Acta. Myol., 25(2):68-72 (2006).
Okazaki et al., "Autoantibodies against cardiac troponin I are responsible for dilated cardiomyopathy in PD-1-deficient mice," Nat. Med., 9:1477-1483 (2003).
Okazaki et al., "Pathogenic roles of cardiac autoantibodies in dilated cardiomyopathy," Trends Mol. Med., 11(7):322-326 (2005).
Pallais et al., "Acquired hypocalciuric hypercalcemia due to autoantibodies against the calcium-sensing receptor," N. Engl. J. Med., 351(4):362-369 (2004).
Pettersson et al., "Antiantobodies to Cardiac Troponin Associate with Higher Initial Concentrations and Longer Release of Troponin I in Acute Coronary Syndrome Patients," Clin. Chem. (2009).
Ruchala et al., "The prevalence of autoantibodies to: myosin, troponin, tropomyosin and myglobin in patients with circulating triiodothyronine and thyroxine autoantibodies (THAA)," Neuro. Endocrinol. Lett., 28(3):259-266 (2007).
Shmilovich et al., "Autoantibodies to cardiac troponin I in patients with idiopathic dilated and ischemic cardiomyopathy," Int. J. Cardiol., 117(2):198-203 (2007; Epub 2006).
Stanley and Amagai, "Pemphigus, bullous impetigo, and the *staphylococcal* scalded-skin syndrome," N. Engl. J. Med., 355(17):1800-1810 (2006).
Stohl and Looney, "B cell depletion therapy in systemic rheumatic diseases: different strokes for different folks?" Clin. Immunol, 121(1):1-12 (2006).
Stummvoll et al., "Immunoadsorption for systemic lupus erythematosus," Atheroscler Suppl., 10(5):110-113 (2009).
Takeda et al., "Structure of the core domain of human cardiac troponin in the Ca(2+)-saturated form," Nature, 424(6944):35-41 (2003).
Vaughan et al., "B cells—masters of the immunoverse," Int. J. Biochem. Cell Biol., 43(3):280-285 (2011).

(Continued)

*Primary Examiner* — Michael Szperka
(74) *Attorney, Agent, or Firm* — Knobbe, Martins, Olson & Bear LLP

(57) ABSTRACT

Provided herein are, inter alia, methods of diagnosing and treating autoimmune cardiomyopathy in subjects, based upon the detection of IgG4 autoantibodies to cardiac troponin I (cTnI).

15 Claims, 10 Drawing Sheets

OTHER PUBLICATIONS

Vienuesa et al., "Dysregulation of germinal centres in autoimmune disease," Nat. Rev. Immunol, 9(12):845-857 (2009).
Wu, Alan, "Cardiac Troponin: Friend of the Cardiac Physician, Foe to the Cardiac Patient?" Circulation, 114:1673-1675 (2006).
Wynne and Braunwalk, "The cardiomyophathies and myocarditides." In: Braunwald E., Zipes D. P., P.L. eds. Heart Disease: A Textbook of Cardiovascular Medicine. $6^{th}$ ed. Philadelphia: WB Saunders Company; 1751-1806 (2001).
Galinska et al., "The C-terminus of cardiac troponin I stabilizes the Ca2+-activated state of tropomyosin on actin filaments." Cerc. Res., 106(4):705-711 (2010).
Khosroshahi et al., "Rituximab Therapy Leads to Rapid Decline of Serum IgG4 Levels and Prompt Clinical Improvement in IgG4-Related Systemic Disease." Arthritis & Rheumatism, 62(6):1755-1762 (2010).
Niebroj-Dobosz et al., "Circulating autoantibodies to troponin I in Emery-Dreifuss muscular dystrophy." Acta Myologica, XXVII: 1-6 (2008).
Soschenko et al., "Endomiocardial Biopsy: The First Experience," Siberian Oncologic Journal. No. 3 (23): 94-96 (2007).
International Search Report and Written Opinion issued in PCT/US2012/038868 dated Aug. 16, 2012 (8 pages).

* cited by examiner

FIG. 6

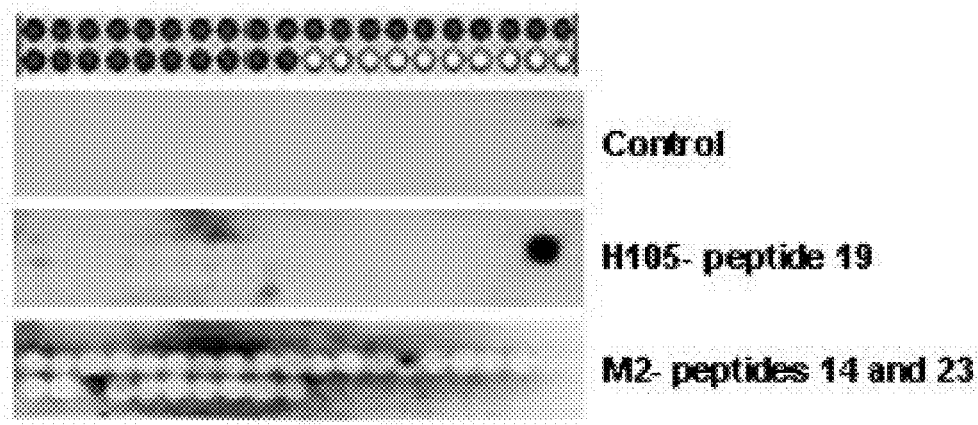

```
P1   MADGSSDAAR  (Residues 1-10 of SEQ ID NO:1)
P2   AAREPRPAPA  (Residues 8-17 of SEQ ID NO:1)
P3   APAPIRRRSS  (Residues 15-24 of SEQ ID NO:1)
P4   RSSNYRAYAT  (Residues 22-31 of SEQ ID NO:1)
P5   YATEPHAKKK  (Residues 29-38 of SEQ ID NO:1)
P6   KKKSKISASR  (Residues 36-45 of SEQ ID NO:1)
P7   ASRKLQLKTL  (Residues 43-52 of SEQ ID NO:1)
P8   KTLLLQIAKQ  (Residues 50-59 of SEQ ID NO:1)
P9   AKQELEREAE  (Residues 57-66 of SEQ ID NO:1)
P10  EAEERRGEKG  (Residues 64-73 of SEQ ID NO:1)
P11  EKGRALSTRC  (Residues 71-80 of SEQ ID NO:1)
P12  TRCQPLELAG  (Residues 78-87 of SEQ ID NO:1)
P13  LAGLGFAELQ  (Residues 85-94 of SEQ ID NO:1)
P14  ELQDLCRQLH  (Residues 92-101 of SEQ ID NO:1)
P15  QLHARVDKVD  (Residues 99-108 of SEQ ID NO:1)
P16  KVDEERYDIE  (Residues 106-115 of SEQ ID NO:1)
P17  DIEAKVTKNI  (Residues 113-122 of SEQ ID NO:1)
P18  KNITEIADLT  (Residues 120-129 of SEQ ID NO:1)
P19  DLTQKIFDLR  (Residues 127-136 of SEQ ID NO:1)
P20  DLRGKFKRPT  (Residues 134-143 of SEQ ID NO:1)
P21  RPTLRRVRIS  (Residues 141-150 of SEQ ID NO:1)
P22  RISADAMMQA  (Residues 148-157 of SEQ ID NO:1)
P23  MQALLGARAK  (Residues 155-164 of SEQ ID NO:1)
P24  RAKESLDLRA  (Residues 162-171 of SEQ ID NO:1)
P25  LRAHLKQVKK  (Residues 169-178 of SEQ ID NO:1)
P26  VKKEDTEKEN  (Residues 176-185 of SEQ ID NO:1)
P27  KENREVGDWR  (Residues 183-192 of SEQ ID NO:1)
P28  DWRKNIDALS  (Residues 190-199 of SEQ ID NO:1)
P29  ALSGMEGRKK  (Residues 197-206 of SEQ ID NO:1)
P30  MEGRKKKFES  (Residues 201-210 of SEQ ID NO:1)
```

DIAGNOSIS AND TREATMENT OF CARDIAC TROPONIN 1 (CTN1) AUTOANTIBODY-MEDIATED HEART DISEASE

FEDERALLY SPONSORED RESEARCH OR DEVELOPMENT

This invention was made with Government support under Grant No. RO1 HL077554 awarded by the National Institutes of Health. The Government has certain rights in the invention.

TECHNICAL FIELD

This invention relates to methods of diagnosing and treating autoimmune mediated heart disease, e.g., cardiomyopathy or cardiac arrhythmias, in subjects.

BACKGROUND

Cardiomyopathy is a disease that weakens and enlarges heart muscle, and can lead to heart failure. Heart failure is the most common hospital discharge diagnosis and accounts in the United States. Dilated cardiomyopathy (DCM) is a relatively common condition (estimated prevalence 1:2500) 36.5 per 100,000 in Olmsted County, Minn. (Cetta and Michels, Ann. Med. 27, 169-173 1995) and is the third leading cause of heart failure. The clinical course of DCM is usually one of inexorable decline punctuated by acute decompensation. As a result, DCM remains the most frequent indication for cardiac transplantation. Despite the high mortality, morbidity and costs associated with DCM, the pathophysiology of this condition is largely unknown, and almost half do not have an identifiable etiology and are labeled as having idiopathic DCM (Felker, G M et al, Medicine 78(4): 270-283, 1999). Current management of DCM provides only supportive therapy rather than treating an underlying cause. As a result, once heart failure is established in a patient with DCM, the expected outcome is poor, with a 5 year mortality of about 46% (Felker et al., The New England journal of medicine. 2000; 342:1077-1084).

SUMMARY

The present invention is based, at least in part, on the discovery of the presence of IgG4 subclass autoantibodies to cardiac troponin I in human patients who have autoimmune heart disease, e.g., arrhythmia and/or cardiomyopathy, and that such patient(s) can benefit from immunotherapy. Accordingly, provided herein are methods for diagnosing and treating autoimmune heart disease in a subject.

In one aspect, provided herein are methods for diagnosing autoimmune heart disease in a subject, the method comprising: providing a sample from a subject who has heart disease; and detecting a level, or the presence or absence, of IgG autoantibodies, e.g., autoantibodies of the IgG1, IgG2, IgG3, or IgG4 subclass to cardiac troponin I (cTnI) in the sample, wherein the presence of the IgG autoantibodies indicates that the subject has autoimmune heart disease. In some embodiments, the methods include determining whether the anti-cTnI antibodies are predominantly (at least 50%, e.g., at least 60%, 70%, 80%, or 90%) IgG4 subclass, wherein the presence of predominantly IgG4 subclass anti-cTnI antibodies indicates that the subject has autoimmune heart disease. In some embodiments, the methods include determining the level of IgG4 subclass autoantibodies to cTnI in the sample, and comparing the level to a reference level, wherein the presence of a level of IgG4 autoantibodies to cTnI above the reference level indicates that the subject has autoimmune heart disease. Reference levels can be determined using epidemiological and biostatistical methods known in the art. For example, the reference level can represent a threshold level, above which a subject has, or has an increased risk of developing, autoimmune heart disease.

In some embodiments, the sample comprises serum from the subject. In some embodiments, the sample comprises cardiac tissue, e.g., from a biopsy sample, e.g., an endomyocardial biopsy sample, and the methods include detecting IgG autoantibodies, e.g., IgG4 subclass specific deposition on the surface of cardiac myocytes from the subject.

In some embodiments, the subject has cardiac arrhythmia or idiopathic dilated cardiomyopathy. In some embodiments, autoantibodies that bind to epitopes within residues 127-164 of human cTnI are detected. In some embodiments, autoantibodies that bind to an epitope within residues 127-136, 92-101, or 155-164 of human cTnI are detected.

In one aspect, methods for treating autoimmune heart disease, the method comprising: selecting a subject who has autoimmune heart disease; and administering to the subject a therapy that depletes B lymphocytes in the subject.

In some embodiments, the subject is selected by detecting the presence of IgG4 autoantibodies to cardiac troponin I (cTnI) in the subject.

In another aspect, the invention provides methods for monitoring the efficacy of a treatment for autoimmune heart disease. The methods include providing a first sample comprising serum of a subject; detecting a level of IgG, e.g., IgG1, IgG2, IgG3, or IgG4, autoantibodies to cardiac troponin I (cTnI) in the first sample, administering a therapy to the subject; providing a subsequent sample comprising serum of a subject; detecting a level of IgG autoantibodies to cTnI in the subsequent sample; and comparing the level of IgG, e.g., IgG4, autoantibodies to cTnI in the first sample to the level of IgG, e.g., IgG4, autoantibodies to cTnI in the subsequent sample. A decrease in level of IgG, e.g., IgG4, autoantibodies to cTnI from the first to the subsequent sample indicates that the therapy is effective.

In some embodiments, the therapy is or includes administration of an effective amount of a treatment that reduces numbers of antibody-producing B cells, e.g., and anti-CD20 antibody, e.g., rituximab; in some embodiments, the therapy is or includes administration of 375 mg/m$^2$ of rituximab i.v. weekly for four weeks. The therapy can also be or include treating the subject with plasmapheresis or administering intravenous immunoglobulin.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention.

The terms "effective amount" and "effective to treat," as used herein, refer to an amount or a concentration of one or more compounds or a pharmaceutical composition described herein utilized for a period of time (including acute or chronic administration and periodic or continuous administration) that is effective for treating autoimmunity-mediated heart disease, e.g., for reducing one or more symptoms or clinical signs, and returning the subject to normal or more normal cardiac function. In addition, in some embodiments the methods of treatment may reduce levels of IgG, e.g., IgG1, IgG2, IgG3, or IgG4 autoantibodies, e.g., circulating levels of IgG autoantibodies.

Effective amounts of one or more compounds or a pharmaceutical composition for use in the present invention include amounts that treat autoimmune-mediated heart disease, e.g., prevent or delay the onset, delay or halt the progression, ameliorate the effects of, or generally improve the prognosis of a subject diagnosed with e.g., autoimmune-mediated heart disease. For example, in the treatment of autoimmune-mediated heart disease, a compound which improves survival or cardiac function, or decreases the level of IgG, e.g., IgG4, autoantibodies to cardiac troponin I to any degree or delays or arrests any symptom of autoimmune-mediated heart disease would be therapeutically effective. Since advanced heart failure with irreversible heart damage may already be present at onset of therapy, a therapeutically effective amount of a compound is not required to cure a disease but will provide a treatment for a disease.

The term "subject" is used throughout the specification to describe an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 6 is dot blot data demonstrating that the autoantibodies found in subjects recognized specific epitopes in human cardiac troponin I protein (SEQ ID NO:1).

DETAILED DESCRIPTION

Figure 1A:
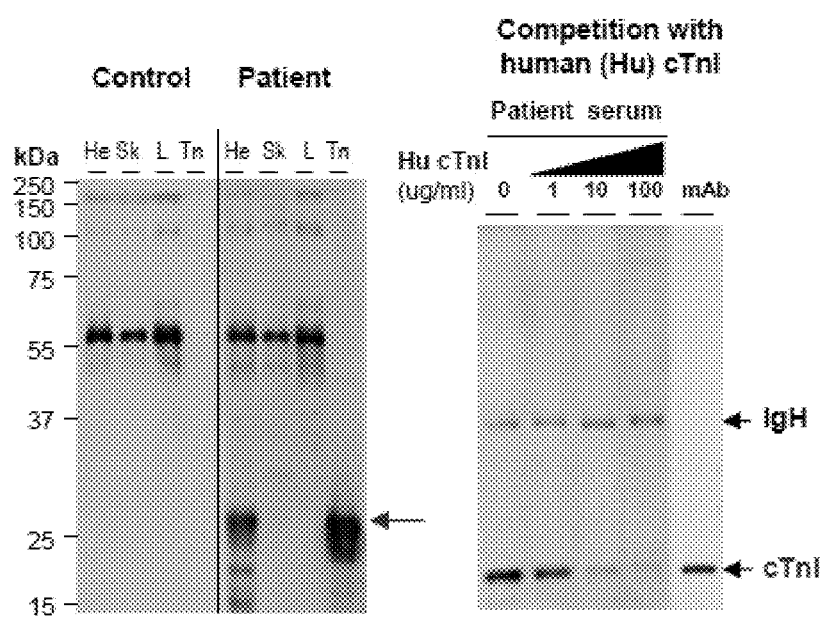
FIG. 1A is a pair of immunoblots showing that a subject with cardiomyopathy had autoantibodies to cardiac troponin I, and that these cTnI autoantibodies can be greatly reduced or removed from the serum by pre-absorption ("competition") with recombinant human troponin I protein.

The importance of autoimmunity in the pathogenesis of heart disease has been uncertain because of a lack of reliable serological assays that can define autoimmune heart disorders with the same sensitivity and specificity that are available for other autoimmune diseases. Data described herein suggest that patients with heart disease who have high-affinity autoantibodies to cardiac troponin I as detected by fluid-phase radioimmunoassay represent a distinct heart failure phenotype that could be treated with immunotherapy, e.g., B-cell targeted immunotherapy.

Accordingly, described herein are methods for diagnosing autoimmune heart disease in subjects by detecting the presence or absence of IgG, e.g., IgG4, autoantibodies to cardiac troponin I (cTnI). Subjects who have been diagnosed as having autoimmune heart disease can be treated with immunotherapy, e.g., the B-cell targeted immunotherapy described herein. Methods for treating autoimmune heart disease are also provided.

IgG4 Subclass Antibodies

IgG4 are the rarest of the human IgG subclasses, accounting for only 3-6% of total serum IgG. They are strongly linked to antibody-mediated autoimmune diseases, e.g., idiopathic membranous nephropathy (Beck et al., N Engl J Med 2009; 361(1):11-21), pemphigus (Bhol et al., Proceedings of the National Academy of Sciences of the United States of America 1995; 92(11):5239-43) and hyperparathyoidism due to antibodies against the calcium-sensing receptor (Pallais et al., N Engl J Med 2004; 351(4):362-9). The target antigens of IgG4-mediated autoimmune diseases are generally expressed on the cell surface or extracellularly where they are accessible to antibodies; for example, in pemphigus, the autoantigen is desmoglein-3 (Stanley and Amagai, N Engl J Med 2006; 355(17):1800-10); in idiopathic membranous nephropathy, the autoantigen is phospholipase A2 receptor (Beck et al., N Engl J Med 2009; 361(1):11-21). IgG4 subclass autoantibodies to cardiac autoantigens have not previously been described in heart failure patients.

Diagnostic Methods

Provided herein are methods for diagnosing whether a subject's heart disease is related to or mediated by autoimmunity. The diagnostic methods include detecting the presence or absence of IgG, e.g., IgG4 autoantibodies to cTnI in a subject who has heart disease. The presence of IgG, e.g., IgG4 subclass autoantibodies to a cardiac autoantigen indicates that the subject has autoimmune heart disease (e.g., cardiac arrhythmia, heart failure, or cardiomyopathy mediated by or associated with the presence of autoantibodies).

In some embodiments, IgG, e.g., IgG4, autoantibodies to specific epitopes within cTnI are detected. For example, autoantibodies that recognize epitopes within residues 127-164 or 92-164 of human cTnI (SEQ ID NO:1) can be detected using, e.g., a peptide comprising residues 127-164 or 92-164 of SEQ ID NO:1. In some embodiments, autoantibodies that recognize an epitope within residues 127-136, 92-101, or 155-164 of human cTnI (SEQ ID NO:1) are detected using, e.g., a peptide comprising residues 127-136, 92-101, or 155-164 of SEQ ID NO:1. Since most bone-fide autoantibody-mediated diseases are characterized by high-affinity autoantibodies to a narrow range of epitopes (Vinuesa et al., Nat Rev Immunol. 2009 Dec; 9(12):845-57), knowledge that subjects have restricted recognition of cTnI is useful in deciding which patients are most likely to be responsive to rituximab.

In some embodiments, an initial screening is done using a full-length cTnI, e.g., in a fluid-phase (e.g., radioimmunoprecipitation assay) format, to detect the presence of anti-cTnI antibodies. This format is preferred to detect high-affinity autoantibodies that are often involved in autoimmune disease. A second screen for IgG, e.g., IgG4, antibodies could then be done, e.g., by Western blotting, radioimmunprecipitation assay, or ELISA.

Once it has been determined that a subject has autoimmune heart disease, the information can be used in a variety of ways. For example, a decision to administer a B-cell specific immunomodulatory treatment, e.g., the treatment described herein, can be made.

The methods described herein are useful in a wide variety of clinical contexts. For example, the methods can be used for diagnosing subjects in hospitals and outpatient clinics, as well as the Emergency Department. The methods can be carried out on-site or in an off-site laboratory.

Cardiac Troponin I

Cardiac troponin I (cTnI) polypeptides or immunogenic fragments thereof and nucleic acids encoding cardiac TnI polypeptides or immunogenic fragments thereof are useful in the methods described herein. Exemplary cardiac TnI amino acid sequences can be found at, e.g., Genbank Accession Nos. NP_000354.4 (human; set forth as SEQ ID NO:1 in FIG. 5) and NP_033432.1 (mouse). Exemplary cardiac TnI nucleic acid sequences can be found at Genbank Accession Nos. NM_000363.4 (human) and NM_009406.3 (mouse). Immunogenic fragments can include amino acids 92-164, 127-164, 127-136, 92-101, or 155-164 of SEQ ID NO:1.

A nucleic acid encoding a mammalian, e.g., human, cTnI amino acid sequence can be amplified from human cDNA by conventional PCR techniques, using primers upstream and downstream of the coding sequence.

One method for producing cTnI polypeptides or fragments thereof for use in the invention is recombinant expression, which typically involves in vitro translation and transcription from a recombinant nucleic acid expression vector encoding a cTnI cDNA or portion thereof. Guidance concerning recombinant DNA technology can be found in numerous well-known references, including Sambrook et al., 2001, "Molecular Cloning—A Laboratory Manual," 3d Ed. Cold Spring Harbor Press; and Ausubel et al. (eds.), 2002, "Short Protocols in Molecular Biology," John Wiley & Sons, Inc.

Purification of recombinant cTnI polypeptides or fragments thereof can be performed by conventional methods and is within ordinary skill in the art. The purification can include two or more steps, and one step can be affinity chromatography employing anti-cTnI antibodies covalently linked to a solid phase chromatography support (beads) such as crosslinked agarose or polyacrylamide. Other useful purification steps include gel filtration chromatography and ion exchange chromatography. Purified cTnI polypeptides and fragments thereof are also commercially available (e.g., from Sigma-Genosys, Biolegend, or Abcam).

Detecting Autoantibodies

Methods known in the art or described herein can be used to detect the presence or absence of IgG, e.g., IgG4 autoantibodies to cardiac autoantigens. In some embodiments, serum samples from subjects are contacted with a cardiac autoantigen, e.g., cTnI or alpha-myosin heavy chain polypeptide, or an immunogenic fragment thereof, for a sufficient amount of time and under conditions that allow binding of the cardiac antigens to any autoantibodies in the serum samples. Binding occurs between the cTnI polypeptide or fragment thereof and the autoantibodies are then detected and, in some embodiments, quantified. In some embodiments, the autoantibodies are isolated and the presence of IgG, e.g., IgG4 subclass antibodies is detected, and, in some embodiments, quantified.

In some embodiments, biopsy samples are contacted with subclass-specific binding reagents, e.g., antibodies that bind specifically to IgG4 (and/or optionally one or more other subclasses, e.g., IgG1, IgG2, or IgG3), and the presence (and optionally, quantity) of IgG4 antibodies.

For example, enzyme-linked immunosorbent assay (ELISA) can be used to detect the presence of autoantibodies in the serum of subjects. ELISA can detect autoantibodies that bind to antigens immobilized on solid support (e.g., a multi-well plate) by using enzyme-linked secondary antibodies, such as goat anti-human Ig Abs, and enzyme substrates that change color in the presence of enzyme-labeled antibodies. Fluid-phase radioimmunoassays (RIA) can also be used to detect the presence of autoantibodies. For example, the gene for the antigen can be cloned into an expression vector, and in vitro translation can be carried out with [$^{35}$S]methionine to produce radiolabeled antigens. Antibody-bound radiolabeled antigens can be separated from free radiolabeled antigens with, e.g., protein A-Sepharose or protein G-Sepharose beads, which bind to the antibodies. To detect the presence of a specific subclass of autoantibodies, e.g., IgG1, IgG2, IgG3 or IgG4 antibodies, anti-IgG1, IgG2, IgG3, or IgG4 antibodies can be used. For example, mouse anti-human IgG4 antibodies (available from, e.g., Sigma) bound to Sepharose beads can be employed in RIA to detect subclass-specific autoantibodies in samples from a human subject using radioactive-labeled antigens and detecting specific immunocomplexes using a liquid scintillation counter. Other methods known in the art or described herein can be used to detect the presence of autoantibodies.

Subjects

The presence of autoimmune heart disease can be detected in a subject with cardiomyopathy, e.g., ischemic, dilated, hypertrophic, idiopathic, or restrictive cardiomyopathy; a subject with unexplained cardiac arrhythmias; or a subject with heart failure, e.g., unexplained heart failure; using methods described herein. Those of ordinary skill in the art would be able to determine whether a subject has cardiomyopathy, cardiac arrhythmia, or heart failure, using methods and knowledge known in the art (see, e.g., Wynne and Braunwald, "The cardiomyopathies and myocarditides." In: Braunwald E., Zipes D. P., P. L, eds. Heart disease: a textbook of cardiovascular medicine. 6th ed. Philadelphia: W.B. Saunders Company; 2001:1751-806).

In addition, the presence of autoimmune heart disease can be detected using the methods described herein in subjects who are asymptomatic, or subjects who are asymptomatic relatives of affected patients.

Therapeutic Methods

Data described herein suggest that a subject who suffers autoimmune-mediated heart disease will benefit from immunotherapy. In particular, these subjects may benefit from agents that target B lymphocytes, which make antibodies. Accordingly, the present therapeutic methods can include selecting a subject who has autoimmune heart disease, and administering to the subject an effective amount of an immunotherapy. In some embodiments, the methods include administering a compound that decreases B lymphocytes, e.g., employing a direct depletion approach by engagement of B cell surface molecules, e.g., CD19, CD20, or CD200, e.g., with an anti-CD20 monoclonal antibody (e.g., rituximab), an anti-CD19 monoclonal antibody (e.g., XmAb5574 (MOR208; Xencor, Monrovia Calif.) or MDX-1342 (Medarex, Princeton, N.J.)), an anti-CD22 monoclonal antibody (e.g., epratuzumab); or an indirect attrition by inhibition of survival by neutralization of B lymphocyte stimulator (BLyS), a potent B cell survival factor (e.g., using anti-BLyS/BAFF agents such as belimumab or atacicept). In some embodiments, the methods include administering, in addition to or as an alternative to rituximab, Azathioprine; a steroid such as cyclosporine or methylprednisolone; Immunoadsorption (IAS)/plasmapheresis. See, e.g., Engel et al., Pharmacol Rev. 2011 March; 63(1):127-56. Epub 2011 Jan. 18; Stohl and Looney, Clin Immunol. 2006 October; 121(1):1-12. Epub 2006 May 11; Stummvoll et al., Atheroscler Suppl. 2009 Dec. 29; 10(5):110-3; and Vaughan et al., Int J Biochem Cell Biol. 2011 March; 43(3):280-5. Epub 2010 Dec. 13.

In patients with rheumatoid arthritis treated with rituximab, clinical relapse was preceded by a rise in autoantibody levels and B cells reappeared at a mean of 8 months after treatment (Leandro et al., Arthritis Rheum 2006; 54(2):613-20). In contrast, in severe pemphigus associated with IgG4 autoantibodies, 86% of subjects treated with rituximab remained in complete remission almost after mean follow-up of 34 months suggesting that in some autoimmune conditions, remissions can be sustained (Joly et al., N Engl J Med 2007; 357(6):545-52). The use of rituximab for cardiomyopathy has not previously been described.

The treatment methods described herein can be combined with other immunotherapy, e.g., plasmapheresis to remove the autoantibodies typically with supplemental administration of intravenous immunoglobulin (IVIg). Two methods are typically used in plasmapheresis to separate plasma from blood cells: membrane filtration and extracorporeal centrifugation. Both techniques are designed to remove large molecular weight substances, such as antibodies, from the plasma. IVIg is a mixture of proteins containing γ-globulins, predominantly IgG, to provide passive, temporary humoral immunity against disease. Other treatments for heart disease can also be administered.

Subject Selection

The present treatments methods can be used to treat subjects who have autoimmune heart disease, e.g., subjects whose heart disease has been diagnosed as mediated by or related to autoimmunity, e.g., by a method described herein. Thus the methods can include detecting the presence of autoimmune heart disease in a subject using a method described herein, and administering to the subject a therapeutically effective amount of an agent described herein, e.g., agents that target B lymphocytes, e.g., rituximab.

Monitoring of Treatment

Effectiveness of the treatment methods described herein can be determined by monitoring changes in the cardiac symptoms, characteristic features, or parameters of the subject being treated. For the methods described herein, it may be useful to monitor the level of IgG, e.g., IgG4, autoantibodies to cTnI in the subject, e.g., before, throughout, and after the treatment. Evaluation by endomyocardial biopsy could include examination for one or both of total IgG and IgG subclass deposition.

Pharmaceutical Compositions and Methods of Administration

The compounds and compositions described herein can be administered to a subject, e.g., a subject identified as being in need of treatment, using a systemic route of administration. Systemic routes of administration can include, but are not limited to, parenteral routes of administration, e.g., intravenous injection, intramuscular injection, and intraperitoneal injection; enteral routes of administration, e.g., administration by the oral route, lozenges, compressed tablets, pills, tablets, capsules, drops (e.g., ear drops), syrups, suspensions and emulsions; transdermal routes of administration; and inhalation (e.g., nasal sprays).

In some embodiments, the modes of administration described above may be combined in any order and can be simultaneous or interspersed.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

The compositions described herein can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For compounds known in the art (e.g., rituximab), practitioners might generally use in humans and non-human subjects the recommended (e.g., FDA approved) dosage for that compound.

EXAMPLES

The invention is further described in the following examples, which do not limit the scope of the invention described in the claims.

Example 1

Identification of IgG4 Autoantibodies to cTnI in Human Patients

Evidence that autoimmune mechanisms alone can cause T1D heart disease is exemplified by a patient with T1D since age 12 yrs ("H-105") who, at age 17 yrs, presented with severe arrhythmias and unexplained dilated cardiomyopathy with normal coronary angiography. The family history was notable for the presence of autoimmune diseases in multiple family members including a parent with T1D and thyroiditis.

A complete clinical evaluation of the patient was performed to define the etiology of his cardiomyopathy, including EKG, chest X-ray, blood work, echocardiography, and cardiac MRI.

Blotting was performed to detect autoantibodies. 2.5 ug/lane of total SDS lysates from human heart, skeletal muscle and liver or 0.25 ug/lane of purified human cTnI (Life Diagnostics) were separated in a 10% SDS-PAGE gel and transferred to nitrocellulose paper. The blots were incubated overnight with control or patient sera diluted 1:1000, followed by incubation with peroxidase-conjugated F(ab')2 fragment of goat anti-human IgG (Jackson ImmunoResearch Laboratories Inc). Blots were developed using Western Lighting Chemiluminescence Reagent Plus (Perkin Elmer). The patient was found to have high titers of autoantibodies directed against cTnI (FIG. 1A).

Figure 1B:
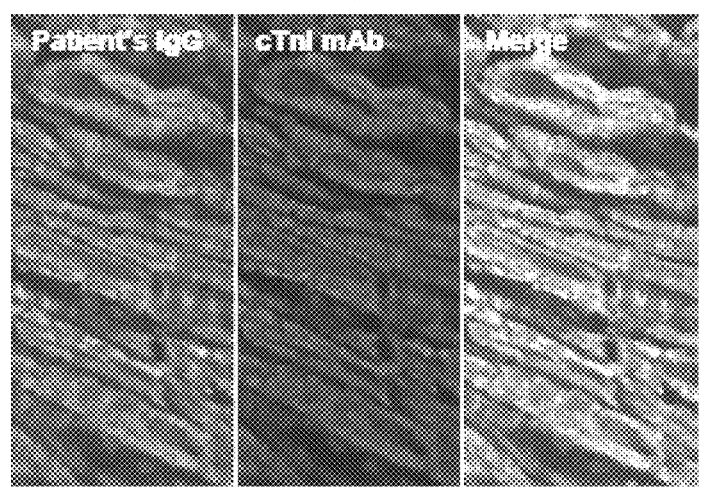
FIG. 1B is a trio of immunofluorescence images showing that serum from the patient shown in 1A (left panel; green in original) stains normal human ventricle muscle tissue in a pattern identical to that of a commercial ventricle monoclonal antibody to cardiac troponin I (shown in the middle panel; red in original). The right panel shows a merged image (yellow in original). These co-localization studies confirm that serum samples from the patient and the anti-cTnI mAb identify the same protein, i.e., cTnI.

Indirect immuno-fluorescent analysis was also performed with the patient's serum. Frozen sections from normal human donor heart embedded in OCT were fixed in 2% paraformaldehyde and permeabilized with TX-100/PBS. After blocking, sections were incubated overnight with 1: 100 dilutions of serum from the patient or 1:250 dilution of mouse monoclonal anti Troponin I (SIGMA), followed by detection with FITC-conjugated mouse F(ab')$_2$ anti-human IgG or FITC conjugated F(ab')$_2$ goat-anti mouse IgG (Jackson ImmunoResearch Laboratories Inc.). For identification of nuclei slides were stained with Hoechst 33258 and mounted using Fluorogel (Electron Microscopy Science). Images were taken with an Axiocam camera linked to a Zeiss Axioscop 2 microscope. The results showed that the patient's autoantibodies stained the surface of normal hearts in a pattern indistinguishable from that seen with a commercial monoclonal antibody against human troponin I (FIG. 1B).

Figure 1C:
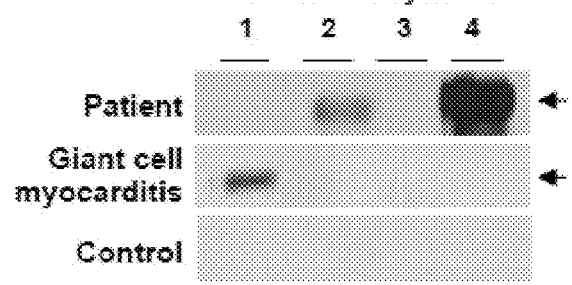
FIG. 1C is an image of an immunoblot showing that, in the same patient shown in FIG. 1A, cTnI autoantibodies are predominantly of the IgG4 subclass (top row). This is in contrast to the expected IgG1 cTnI autoantibodies from a patient with giant-cell myocarditis, which is considered to be primarily a T-cell mediated autoimmune condition (shown in the middle row). No autoantibodies were detected in healthy control serum.

The circulating (serum) anti-troponin antibodies were subjected to subclass analysis as follows. 0.25 ug/lane of purified human cTnI (Life Diagnostics) were separated in a 10% SDS-PAGE gel and transferred to nitrocellulose paper. The blots were cut into strips and incubated with patients or controls sera diluted 1:1000. Individual strips were incubated with mouse antibodies against the four human IgG subclasses (Zymed laboratories). Blots were developed using Western Lighting Chemilumineiscence Reagent Plus (Perkin Elmer) The results showed that the antibodies were predominantly of the IgG4 subclass (FIG. 1C).

Standard hematoxylin and eosin staining of an endomyocardial biopsy revealed the anticipated myocyte hypertrophy and interstitial fibrosis compatible with an advanced cardiomyopathy. No other etiology was identified by the biopsy to account for the patient's condition, including myocarditis or iron deposition.

Figure 1D:
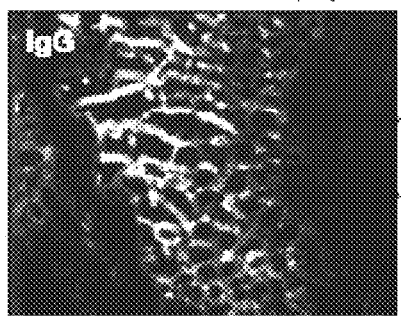
FIG. 1D shows that although IgG4 is a rare subclass and comprised only 3.4% of the patient's total circulating IgGs (data not shown; normal range of serum IgG4=3-6% of total IgG), the patient's cardiac immune deposits contained predominantly IgG4-subclass antibodies.
Figure 1D:
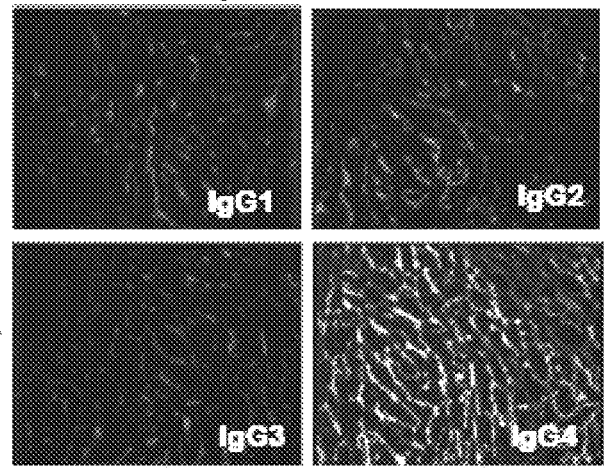

The patient's endomyocardial biopsy sample was frozen in OCT and sections were stained with mAbs against human total IgG and IgG1, IgG2, IgG3 and IgG4. Human cardiac tissues from biopsy were fixed overnight in Paraformaldehyde-glutaraldehyde fixative. The tissue was cryoprotected and embedded in OCT compound (Tissue-Tek, Sakura Finitek). Although IgG4 comprised only 3.4% of his total circulating IgG using subclass-specific antibodies (Human IgG Subclass Profile ELISA kit form Zymed Laboratories INC, following the manufacturer's instructions; normal range of IgG4=3-6%), the patient's heart biopsy sample demonstrated enriched IgG4-specific Ab deposition (FIG. 1D).

Figure 1E:
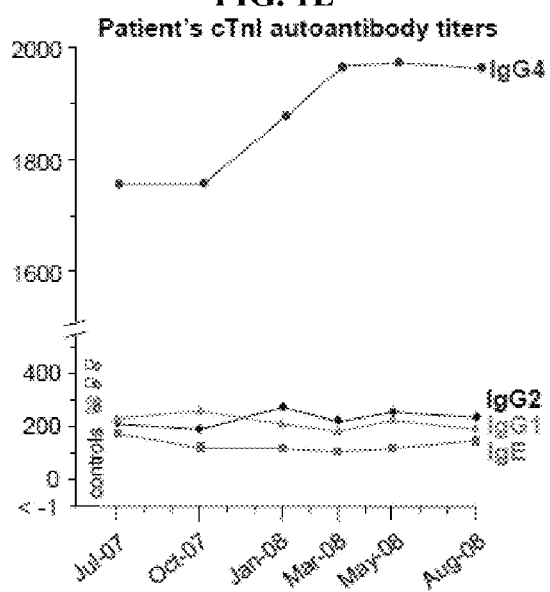
FIG. 1E shows that the patient's IgG4 autoantibody titers increased over time; this was consistent with the worsening disease and decrease in cardiac function seen clinically.
Figure 1F:
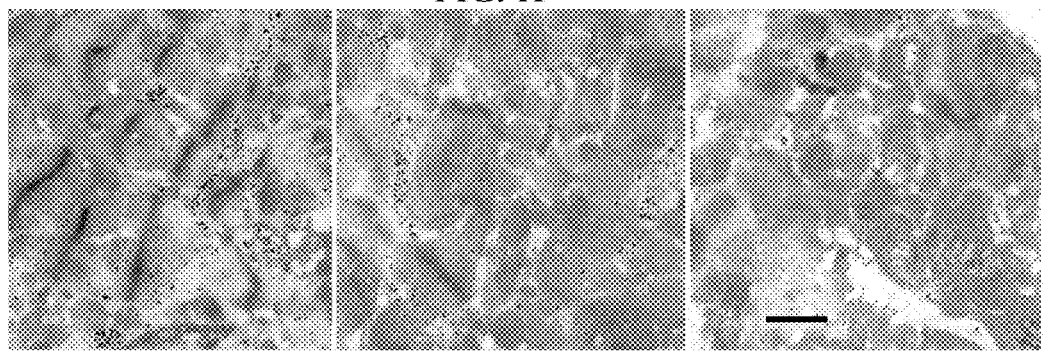
FIG. 1F is a photomicrograph showing immunogold staining of IgG autoantibodies deposited on tissue from an endocardial biopsy from subject H105 (left and middle) and control stain (right).

IgG subclass specific cTnI antibodies were measured by incubating patients or controls serum with $^{35}$S-labeled human cardiac troponin I in TBS −1% TX100 Buffer at 4° C. for 24 h. IgG subclass specific Ab bound Sepharose beads were prepared using Biotin-labeled mouse mAbs against human IgG1, IgG2, IgG4 and IgE (BD Pharmingen) and Sepharose 4B streptavidin beads (GE Healthcare). Aliquots of serum were spotted in a 96-well filtration plate (Unifilter, Whatman) and IgG subclass specific Ab beads were added and incubated for 1 h at 4° with shaking. After incubation the plate was washed with cold TBS-TX-100 buffer, dry and 50 ul of scintillation liquid added. The radioactivity in the samples was determined using a Wallac MicroBeta Scintillation Counter (Perkin Elmer). Interestingly, worsening heart function with a progressive decrease in the patient's ejection fraction from ~50% to ~30% correlated with increasing cTnI-Ab IgG4 titers over a 15-month period (FIG. 1E).

Example 2

Human Patient-Derived cTnI Autoantibodies Recognize TnI on the Plasma Membrane of Heart Cells Specialized biochemical membrane fractionation techniques were performed as described in Head et al., JBC 281 (36) 26391-26399 (2006). Briefly, mouse hearts were homogenized in ice-cold Buffer A (250 mM sucrose, 20 mM Tri-HCl pH 7.4, containing freshly added protease inhibitors) using a 40 ml glass Dounce homogenizer. The homogenate was centrifuge at 700 g×20 min and the resulting supernatant (SN1) was centrifuged at 100,000×g for 1 h. After centrifugation the pellet was resuspended in 500 mM NaHCO$_3$ pH 11 using a glass homogenizer and mixed with 1 volume of 90% sucrose in MBS buffer (25 mM MES pH 6.5, 150 mM NaCl), and layered on a discontinuous sucrose gradient (45, 35 and 5% sucrose in MBS buffer). After centrifugation at 280,000×g for 18 h at 4° C., 1 ml samples were collected from the top of the gradient and analyzed by Western Blotting using the following antibodies: mouse anti-caveolin 3 (BD Transduction Laboratories), rabbit polyclonal anti ATPase beta1 (Na+/K+) (GeneTex, Inc.), mouse anti human cTroponin I (clone C-4) (Santa Cruz Biotechnology Inc.), rabbit anti human c Troponin C (clone H110) (Santa Cruz Biotechnology, Inc.) and patient purified IgG4. The cholesterol concentration for each sample was determined using the Amplex Red Cholesterol Assay Kit (Invitrogen). A band corresponding to cTroponin I was detected in the buoyant caveolin-3 enriched membrane fractions (Fraction No. 5), were also co-localized with the plasma membrane marker ATPase beta1 ($Na^+/K^+$) that was enriched in cholesterol. Cardiac troponin I was also distributed in heavy/non buoyant fractions (Fractions 8-12) and co-localized with cTroponin C. Patient sera recognized the same antigen as the commercial antibody against cTroponin I.

Figure 2A:
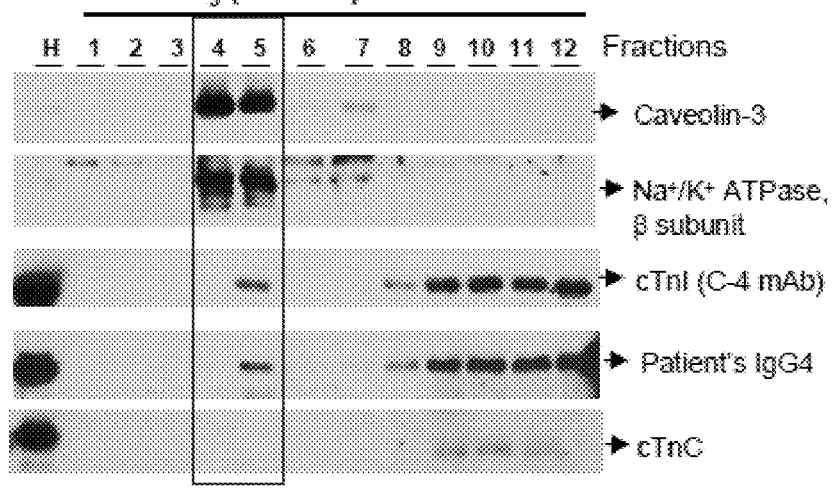
FIG. 2A is an immunoblot (top) and cholesterol assay (bottom) showing the biochemical localization of TnI to a cardiomyocyte lipid-rich membrane fraction (#5) rich enriched in caveolin 3, Na/K ATPase and other signaling proteins that play a crucial role in cardiac contractility.
Figure 2B:
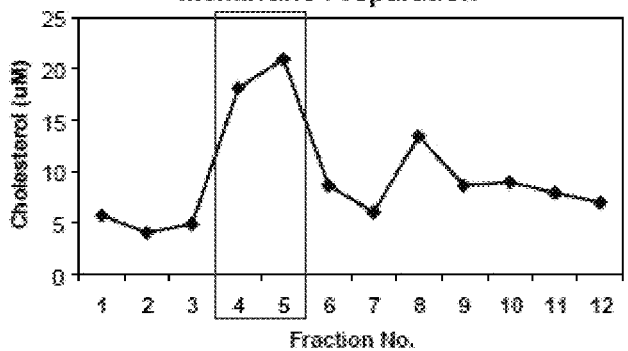
FIG. 2B is an immunoblot showing that the patient's cTnI can immunoprecipitate cTnI from the same membrane fraction #5 isolated from heart cells.
Figure 2B:
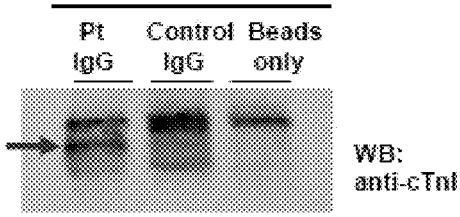

FIG. 2B Fractions enriched in cTnI from the $NaHCO_3$ fractionation protocol were used for immunoprecipitation analysis. Fraction 5 was diluted in MES buffer plus protease inhibitors (0.8 mg protein) and incubated overnight with the patient, control sera or buffer and then with protein A/G plus beads (Pierce). The immunocomplexes bound to the beads were separated in a 4-15% gradient SDS-PAGE gel, transferred to nitrocellulose and probed by western blot (WB) with mouse anti human cTroponin I (clone C-4) (Santa Cruz Biotechnology Inc.). Patient sera but not control sera specifically immunoprecipitated the cTroponin I present in the caveolin enriched fraction obtained by carbonate fractionation.

The results demonstrated that troponin I is found on the plasma membrane of heart cells, in addition to its expected location inside heart cells (FIGS. 2A and 2B). These results are also consistent with immunofluorescence staining and immunogold EM studies clearly deposition of IgG4 autoantibodies on the surface of his myocardial cells.

Example 3

Human Anti-TnI IgG4 Autoantibodies Impair Cardiac Function cTnI Abs have been shown to cause arrhythmias and dilated cardiomyopathy in mouse models (Okazaki et al., Nat Med 9, 1477-83 (2003)), raising the possibility of a similar pathogenic process in this patient. "Pathogenicity assays" (functional assays) were performed. Myocytes from adult rats were obtained by Langendorff-perfusion with $Ca^{2+}$ free Tyrode's solution. Myocytes were culture and treated for 18 h with control or patient sera. $Ca^{2+}$ transients and mechanical properties were assessed in the myocytes, which were continuously perfused in a heated chamber with perfusion buffer (137 mM NaCl, 5.4 mM KCl, 0.5 mM $MgCl_2$, 10 mM HEPES, 5.5 mM glucose, 1.2 mM $CaCl_2$, 0.5 mM probenecid) and electrically stimulated at 0.5 Hz. Cell shortening was monitored by a digital edge detection system (IonOptix) with a sampling rate of 240 Hz. $Ca^{2+}$ transients were measured in fura-2/AM (Molecular Probes) loaded cardiomyocytes (1 uM for 15 min at room temperature) using a dual excitation Hyperswitch (IonOptix). Data were analyzed using the software Ionwizard (IonOptix).

Figure 2C:
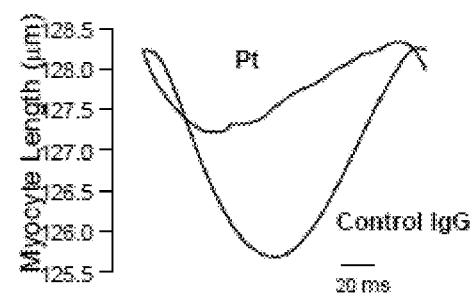
FIG. 2C is a line graph of myocyte length and a pair of bar graphs showing contractility and calcium transients in the presence ("Pt") or healthy control ("Control") immunoglobulins. Treatment with the patient's autoantibodies impaired the contractility of isolated cardiomyocytes.
Figure 2C:
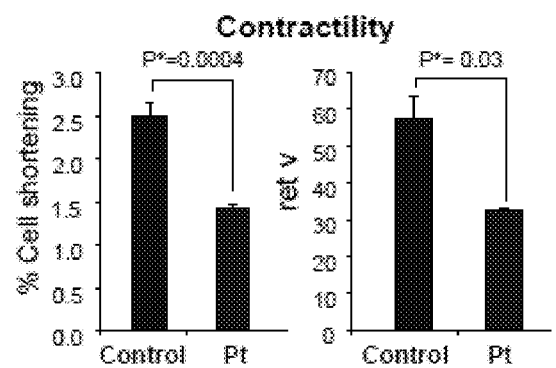
Figure 2C:
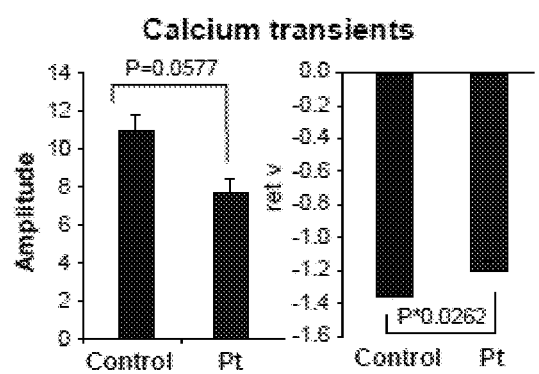

These studies were performed in infusion chambers, visualizing heart beats of adult mouse (or rat) heart cells with the IonOptix video detection system. The results showed that autoantibodies from patient H-105 impaired the contractility and calcium homeostasis of isolated heart cells (FIG. 2C).

Example 4

B-cell Depletion Therapy for Treatment of Autoimmune Heart Disease

Figure 3A:
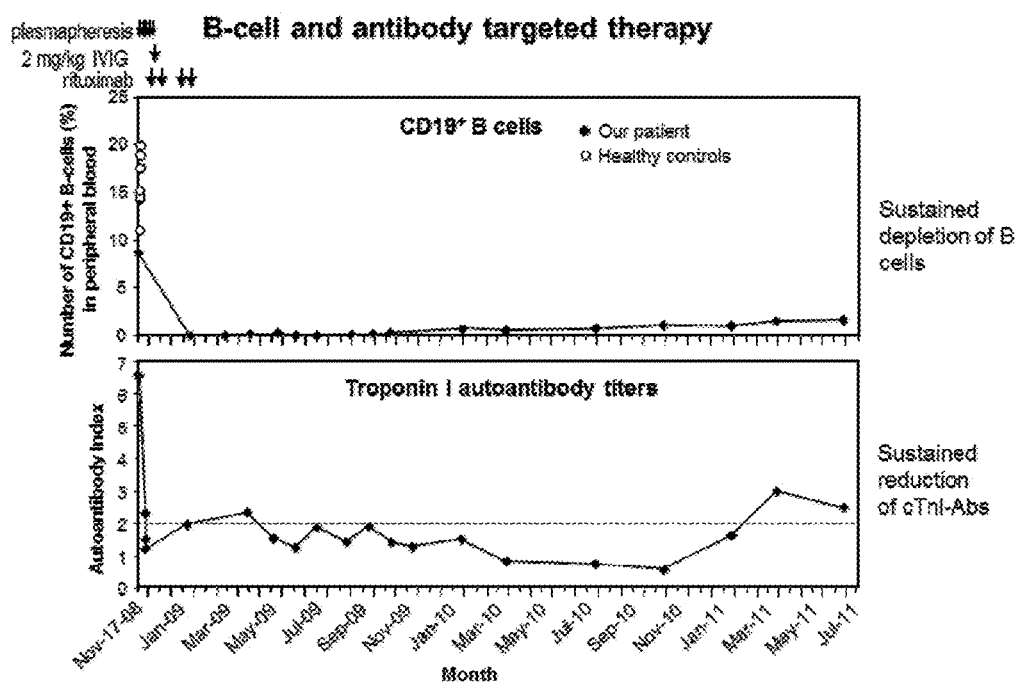
FIG. 3A is a pair of line graphs showing the changes in B cell numbers and cTnI autoantibody titers in response to Rituximab therapy administered in November-December 2009.

Patient H105 completed five cycles of plasmapheresis followed by administration of 2 g/kg intravenous immunoglobulin (IVIG). The patient was subsequently treated with rituximab (375 mg per square meter of body surface area) weekly for a total of four weeks. Two years after this treatment the patient was rated as New York Heart Association Class II with regard to congestive heart failure symptoms and displayed an oxygen consumption of 19.4 ml/kg/min despite a sub-maximal effort as demonstrated by his respiratory ratio of 0.99. The patient's estimated pulmonary artery pressure has remained below 20 mmHg subsequent to completion of his therapy. The rituximab therapy has had a beneficial effect on the patient's anti-troponin I antibody titers. The treatment has also has markedly improved this patient's symptoms and arrested the previously rapid progression of his heart failure with stabilization in his ejection fraction and improvement of his oxygen consumption to 28 ml/kg/min (at his last examination in June, 2011). There was efficient depletion of all subpopulations of peripheral B cells, including cells with plasma cell precursor phenotype ($CD19^+$, $CD20^-$, $CD38^{+++}$) one month after completing his treatment with rituximab, and this has persisted 26 months post-therapy as has the reduction in his anti-troponin antibodies (FIG. 3A). This has been associated with a stabilization in his ejection fraction to 25-30% (after a steady decline from 44% to 31% over the 2-yr period preceding immunotherapy) and improvement in his clinical symptoms.

Figure 3B:
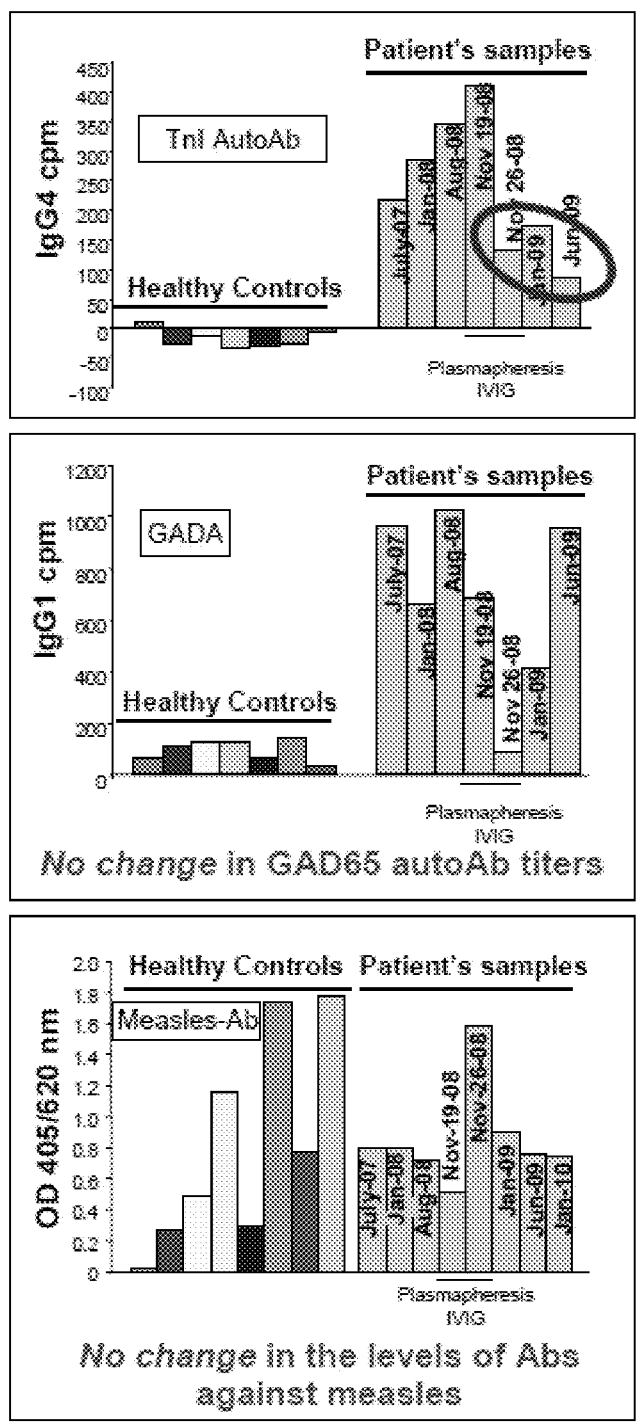
FIG. 3B is a trio of bar graphs showing that Rituximab therapy, administered in November-December 2009 resulted in a sustained decrease in the patient's anti-cTnI IgG4 autoantibodies (top graph), but did not affect his GAD65 (IgG1) autoantibodies (middle graph) or protective anti-measles antibodies (bottom graph).
Figure 4:
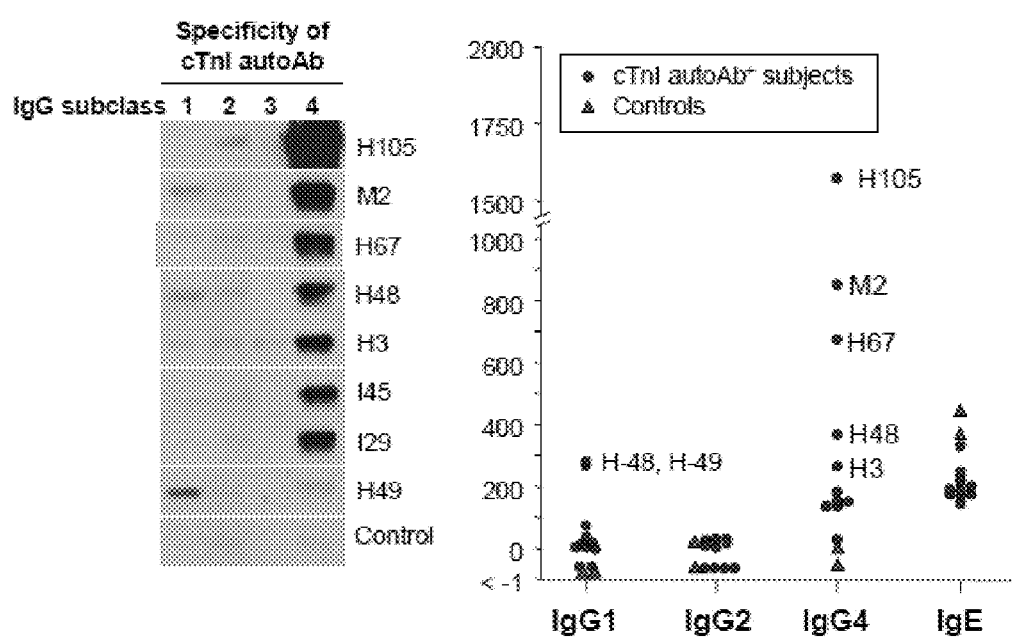
FIG. 4 is a western blot and a dot plot showing that the TnI autoantibody-positive patients contain autoantibodies that are predominantly of the IgG4 subclass. As expected these autoantibodies are not detected in serum from healthy control subjects.

Importantly, the rituximab therapy selectively depleted TnI autoantibodies in subject H105, but did not diminish the levels of either his type 1 diabetes-associated GAD 65 autoantibodies (GADA), which are not postulated to play a pathogenic role in diabetes, or the levels of his protective antibodies to measles (FIG. 3B). The preservation of anti-microbial immunity may explain the lack of any adverse side-effects (i.e., no increased susceptibility to infections) from immunotherapy. These studies suggest that rituximab therapy selectively depletes the B cells that produce pathogenic troponin autoantibodies and underscores the safety and therapeutic potential of using rituximab for patients with idiopathic cardiomyopathy who test positive for troponin I autoantibodies. The ability of rituximab to selectively reduce the patient's IgG4 TnI autoantibodies suggests that they are derived from short-lived autoreactive plasma cells: Selective autoantibody depletion is noted after rituximab treatment in other IgG4-Ab human autoimmune diseases (e.g., pemphigus, Joly et al., N Engl J Med 2007; 357:545-52) and in autoantibody-mediated autoimmune mouse models (Huang et al., Proc Natl Acad Sci USA. 2010 Mar. 9; 107(10):4658-63. Epub 2010 Feb. 22).

Example 5

Screening Human Patients for Autoantibodies to cTnI

New screening assays using recombinantly produced human cTnI protein in a fluid-phase format, suitable for the detection of high affinity autoantibodies characteristic of organ-specific autoimmune diseases, were developed and used to screen a cohort of cardiomyopathy patients.

1. Construction of Recombinant Human cTnI:—

Total RNA was extracted from human ventricle tissue using Trizol (Invitrogen, USA) as per the manufacture's instructions. One microgram of Total RNA was used to reverse-transcribe (RT-PCR) into cDNA using Transcriptor first strand cDNA synthesis kit (Roche, USA) according to the manufacture's protocol.

The cDNA specific to human cardiac troponin I (cTnI) was made by PCR (FastStart High Fidelity PCR system, Roche, USA) using the following specific primers: Forward: 5' TTG CAC TCG TCT AGA TGT CCT CGG GGA GTC TCA AGC 3' (SEQ ID NO:2) and Reverse: 5' TAC CAC GCG TCT AGA AGC TCA GAG AGA AGC TTT ATT 3'(SEQ ID NO:3). Restriction sites for XbaI (underlined in the primer sequences) were incorporated into the forward and reverse primers in order to allow sub-cloning of the PCR products into pSP64 Poly(A) expression vector (Promega, USA) and the subsequent expression of the human cTnI cDNA from the SP6 promoter present in the vector.

One hundred nanograms of cDNA were subjected to 35 cycles of PCR amplification in a Peltier Thermal Cycler (Bio-rad, USA) using the following conditions: denaturation 95° C. for 30 sec, annealing 67.4° C. for 30 sec, elongation 72° C. for 1 min. The PCR products (~837 bp) were ran on 1% agarose gel and then purified using Qiaquick gel purification kit (Qiagen, USA). Subsequently, the purified PCR products were digested with XbaI (New England Biolabs, USA) and then ligated into pSP64 Poly(A) vector at XbaI site. The ligation reaction was transformed into Top 10 competent cells (Invitrogen, USA) and selected the clones by plating them onto LB agar plates containing ampicillin (Sigma) at 100 µg/ml. Successful clones were screened for by restriction digestion with HindIII (New England Biolabs, USA) and the appropriate recombinant plasmids were sequenced completely to verify that no sequence errors had been introduced and also to confirm the orientation of the clone in order to express in vitro from SP6 promoter. The recombinant plasmid, pSP64 Poly(A)+human cTnI, was purified with a QIAGEN Plasmid Maxi Kit (Qiagen, USA). This recombinant plasmid clone was used for the expression of human cTnI protein in a cell free system.

2. Expression of Human cTnI using Cell Free System:—

The plasmid construct (pSP64Poly(A)+human cTnI) was used in a TnT SP6 Quick Coupled Transcription/Translation System (Promega, USA) to produce and label cTnI with [$^{35}$S]-methionine in vitro. The cTnI cDNA fragment was inserted into pSP64 Poly(A) in the correct orientation to allow expression from the SP6 promoter, and each template contained appropriate start and stop codons to ensure accurate translation. A standard reaction mixture of 50 µl contained: quick master mix, 40 µl; plasmid template, 2 µg; [$^{35}$S]-methionine (1000 Ci/mmol; 10 mci/ml; GE Healthcare, USA), 2 µl and made the total volume up to 50 µl with the nuclease free water. The reaction was incubated for 90 minutes at 30° C. and then stored at −20° C. until required.

An aliquot of each of the in vitro translation reaction mixtures was added to SDS sample buffer and boiled for 5 minutes before it ran on 10% Sodium dodecyl sulphate-polyacrylamide gel electrophoresis (SDS-PAGE). Prior to drying under vacuum, gels were soaked in fixing solution and then in 10% glycerol. Autoradiography was carried out at −80° C. Radioactivity incorporated into the protein was determined by trichloroacetic acid (TCA) precipitation as per the Promega's technical manual.

3. Radioimmunoprecipitation Assay for the Detection of Human cTnI Autoantibodies Patient and control sera were tested for binding to [$^{35}$S]-human cTnI in radio-immunoassays as follows. For each assay, an aliquot of in vitro translation reaction mixture (equivalent to 48,000 counts per minute (cpm) of TCA-precipitable material) was suspended in 120 µl of immunoprecipitation buffer containing: 20 mM Tris-HCl pH 7.4; 150 mM NaCl; 1% (v/v) Triton X-100; 10 µg/ml aprotinin (Sigma, USA). Serum was then added to a final dilution of 1:25 and the reaction was carried out in a microcentrifuge tube. The samples were incubated with shaking at room temperature for 2 hrs prior to overnight incubation with shaking at 4° C. All samples were tested in duplicates.

On the next day, 50 µl (20,000 cpm) of the reaction samples were transferred to each well of the 96 well plate (Whatman, USA). Subsequently, 50 µl of protein A/G (50% A/8% G) Sepharose 4 Fast Flow beads (GE Healthcare, USA), prepared according to the manufacturer's protocol, were added to each well and incubation continued for 1 hour at 4° C. The protein A/G Sepharose-antibody complexes were then washed total of twelve times (4 times washing with 5 minutes incubation period in between wishes) in immunoprecipitation buffer at 4° C. with vacuum-operated 96-well plate washer (Millipore, USA). At the end of final wash, the plate was dried under lamp for 10 min and then added 100 µl of MicroScint-20 scintillation cocktail (PerkinElmer, USA) into each well. Immunoprecipitated radioactivity was counted in a Wallac 1450 microbeta Trilux liquid scintillation counter (PerkinElmer, USA). All samples were analyzed in duplicate and the mean cpm immunoprecipitated were determined.

The binding reactivity of each patient and control sera to human cTnI was expressed as an antibody index calculated as: cpm immunoprecipitated by tested serum divided by mean cpm immunoprecipitated by all healthy control sera. The upper level of normal for each assay was calculated using the mean antibody index+3 standard deviations (SD) of all control sera. Patient sera with an antibody index greater than the upper level of normal were regarded as positive for binding to the radio-labeled cTnI used in the assay.

Figure 5:
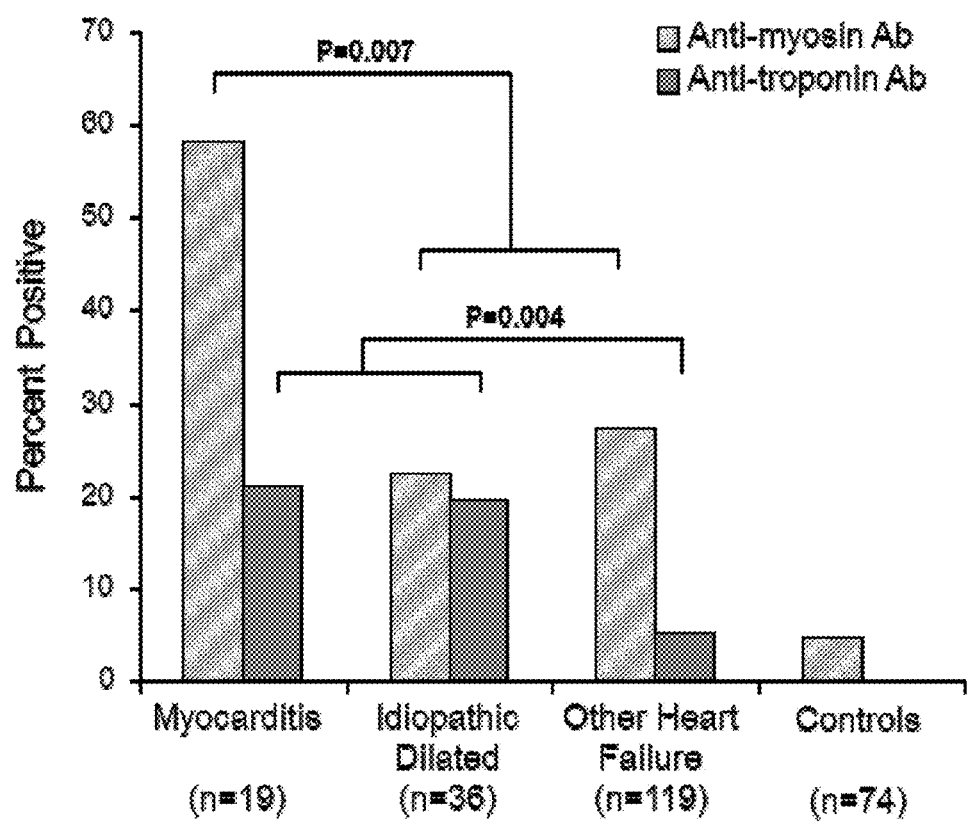
FIG. 5 is a bar graph showing detection of autoantibodies to cardiac myosin or troponin I in a cohort of cardiomyopathy patients.

In the heart failure cohort screened, about 20% of patients with idiopathic dilated cardiomyopathy (DCM) were positive for high-titer autoantibodies directed against cTnI (FIG. 5). Remarkably, these patients were also distinctive in producing predominantly IgG4 subclass anti-cTnI antibodies. Initial characterization of the fine specificities of the autoantibodies revealed that they target the same domain of the cTnI protein. Patients with DCM and high circulating anti-cTnI antibodies may represent a distinct heart failure phenotype that could respond to B-cell targeted immunotherapy.

Mean age was 48 yrs, 61% were male, and mean EF was 30% in HF patients. Anti-troponin Ab were detected more often in myocarditis and idiopathic dilated cardiomyopathy compared to other HF etiologies (20% vs. 5%, p=0.004); none were found in controls. In HF patients, anti-myosin Ab were more common than anti-troponin Ab (29% vs. 10%, p<0.0001) and were particularly enriched in myocarditis subjects vs. other causes of HF (p=0.007). There was little overlap between anti-myosin and anti-troponin Ab production, with 87% of Ab-positive subjects having only a single Ab type detected. See FIG. 5, suggesting that the detection of cTnI autoantibodies defines a unique heart failure phenotype.

Cardiac autoantibodies are relatively common in HF; however, their antigenic specificity varies with etiology. Troponin Ab are more specific to both myocarditis and idiopathic dilated cardiomyopathy. Differential Ab detection may be a marker or mediator of clinical risk in a subset of inflammatory cardiomyopathies.

Example 6

Epitope Analysis for Autoantibodies to cTnI

As a first step towards identifying the epitopes recognized by cTnI autoantibodies in our patients, SPOTscan analysis Epitope mapping protocol was performed as described in the company manual (JPT Peptide Technologies, Germany) was used. This method has been widely used in epitope mapping of autoantigens in other human autoimmune diseases, such as SLE and Goodpasture's syndrome.

Affinity-purified IgGs from H105 and M2 (a 21-year old patient who presented in severe heart failure with an EF of 15% and showed the second highest levels of IgG4 cTnI antibody titers of the cohort studied, see Example 5) were immunoblotted on Whatman 50 cellulose membranes that contained 30 covalently-bound overlapping 10-mer peptides (P1-P30) covering the entire length of the human cTnI protein sequence (SEQ ID NO:1; Sigma-Genosys) (FIG. 6), as follows:

sequences are distinctive in being highly conserved across species (90-100% conservation between rodents and humans), consistent with their important physiological roles: peptides P14 (residues 92-101 of SEQ ID NO:1) and P19 (residues 127-136 of SEQ ID NO:1) are both part of the H2 helix (residues 90-135 of cTnI) that binds to troponin T whereas P23 (residues 155-164 of SEQ ID NO:1) is part of the H3 helix that binds to troponin C (Takeda et al., Nature 2003;424(6944):35-41). Interestingly, sequence motifs residing in the H2 helix have also been recently implicated in a TnI-immunization induced model of murine myocarditis (Kava et al., Circulation 2008;118(20):2063-72).

Immunoassays for autoantibodies based on in vitro translation of cDNAs encoding human cardiac myosin and troponin and immunoprecipitation were also tested with patient sera in 96-well filtration plates. Study subjects (174 with heart failure (HF) and 74 controls) underwent comprehensive evaluation and testing for autoantibodies and HLA-DQ/DR haplotype. HF etiology was assigned by investigators blinded to autoimmune test results. Primary analysis compared specific autoantibodies (Ab) according to HF etiology.

Using troponin peptide mapping techniques, the precise epitopes recognized by autoantibodies from 7 other individuals with high titers of troponin I autoantibodies were identified. Interestingly, one patient (who also had type 1 diabetes) targeted the same peptide as did patient H105 (P19: residues 127-136 of SEQ ID NO:1), while 4 of 8 patients reacted most strongly to a single peptide, P23 (residues 155-164 of SEQ ID NO:1), and 7 of 8 patients recognized peptides spanning peptides 19-23 (residues 127-164 of SEQ ID NO:1). Thus, the autoantibodies from our cohort targeted a similar region of the TnI protein. These findings are important because in other autoimmune diseases, the pathogenicity of autoantibodies correlates closely with the epitopes targeted by autoantibodies (Bhol et al., Proceedings of the National Academy of Sciences of the United States of America 1995; 92(11):5239-43).

```
                                                         (SEQ ID NO: 1)
    P1              p3           p5              p7             p9
madgssdaareprpapapirrrssnyrayatephakkkskisasrklqlktlllqiakqe
          p2              p4           p6             p8 p9           p11          p13          p15            p17
lereaeerrqekqralstrcqplelaqlgfaelqdlcrqlharvdkvdeerydieakvtk
         p10          p12          p14          p16           p18 p17         p19          p21          p23           p25
niteiadltqkifdlrqkfkrptlrrvrisadammqallgarakesldlrahlkqvkked
   p18          p20          p22          p24            p26 p27          p29
tekenrevgdwrknidalsgmegrkkkfes
p26          p28          p30
```

These studies were remarkable in revealing that H105's autoantibodies are essentially monospecific, recognizing only a single peptide, P19 (residues 127-136 of SEQ ID NO:1), whereas M2 serum recognized P14 (residues 92-101 of SEQ ID NO:1) and P23 (residues 155-164 of SEQ ID NO:1) Sera from normal controls did not react with any of the cellulose-bound cTnI peptides (FIG. 6). These peptide Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing the presence of, or risk of developing, autoimmune heart disease in a subject, the method comprising:
 providing a sample comprising serum of a subject; and
 performing an assay to detect a level, presence, or absence in the sample of IgG4 autoantibodies to cardiac troponin I (cTnI), wherein the presence of IgG4 autoantibodies to cTnI indicates that the subject has or is at risk of developing autoimmune heart disease;
 selecting a subject who has or is at risk of developing autoimmune heart disease; and
 administering to the subject a therapy for autoimmune heart disease.

2. The method of claim 1, wherein the subject has cardiac arrhythmia, idiopathic dilated cardiomyopathy, ischemic cardiomyopathy or unexplained heart failure.

3. The method of claim 1, wherein autoantibodies that bind to an epitope within residues 92-164 of SEQ ID NO:1 are detected.

4. The method of claim 3, wherein autoantibodies that bind to epitopes within residues 92-101, 127-136, or 155-164 of SEQ ID NO:1 are detected.

5. A method for diagnosing the presence of, or risk of developing, autoimmune heart disease in a subject, the method comprising:
 providing a sample comprising cardiac tissue of a subject; and
 performing an assay to detect deposition of IgG4 autoantibodies to cardiac troponin I (cTnI), on cardiac myocytes in the sample,
 wherein the deposition of IgG4 autoantibodies to cTnI indicates that the subject has or is at risk of developing autoimmune heart disease;
 selecting a subject who has or is at risk of developing autoimmune heart disease; and
 administering to the subject a therapy for autoimmune heart disease.

6. The method of claim 5, wherein the sample is an endomyocardial biopsy.

7. The method of claim 5, wherein the subject has cardiac arrhythmia, idiopathic dilated cardiomyopathy, ischemic cardiomyopathy or unexplained heart failure.

8. The method of claim 5, wherein autoantibodies that bind to an epitope within residues 92-164 of SEQ ID NO:1 are detected.

9. The method of claim 8, wherein autoantibodies that bind to epitopes within residues 92-101, 127-136, or 155-164 of SEQ ID NO:1 are detected.

10. The method of claim 1, wherein the therapy depletes or inactivates B lymphocytes in the subject.

11. The method of claim 10, wherein the therapy comprises administration of an effective amount of rituximab or other B-cell depleting or B-cell inactivating agents.

12. The method of claim 10, wherein the therapy comprises treating the subject with plasmapheresis or administering intravenous immunoglobulin.

13. A method for monitoring the efficacy of a treatment for autoimmune heart disease, the method comprising:
 providing a first sample comprising serum of a subject;
 performing an assay to detect a level of IgG4 autoantibodies to cardiac troponin I (cTnI) in the first sample,
 administering a therapy for autoimmune heart disease to the subject;
 providing a subsequent sample comprising serum of the subject;
 performing an assay to detect a level IgG4 autoantibodies to cTnI in the subsequent sample;
 comparing the level of IgG4 autoantibodies to cTnI in the first sample to the level of IgG4 autoantibodies to cTnI in the subsequent sample,
 wherein a decrease in level of IgG4 autoantibodies to cTnI from the first to the subsequent sample indicates that the therapy is effective.

14. The method of claim 13, wherein the therapy comprises administration of an effective amount of rituximab or other B-cell depleting or B-cell inactivating agents.

15. The method of claim 13, wherein the therapy comprises treating the subject with plasmapheresis or administering intravenous immunoglobulin.

* * * * *

SEQUENCE LISTING

<160> NUMBER OF SEQ ID NOS: 3

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
 1               5                  10                  15

Ala Pro Ile Arg Arg Ser Asn Tyr Arg Ala Tyr Ala Thr Glu
            20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

<210> SEQ ID NO 2
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 2
ttgcactcgt ctagatgtcc tcggggagtc tcaagc                                36

<210> SEQ ID NO 3
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 3
taccacgcgt ctagaagctc agagagaagc tttatt                                36